(12) United States Patent
Patil et al.

(10) Patent No.: US 12,141,011 B1
(45) Date of Patent: Nov. 12, 2024

(54) WEARABLE DEVICE BODY DETECTION

(71) Applicant: Amazon Technologies, Inc., Seattle, WA (US)

(72) Inventors: Vashishtha Rajendra Patil, San Francisco, CA (US); John Hubberts, Seattle, WA (US); Dinesh Rajasenan Nair, San Jose, CA (US)

(73) Assignee: Amazon Technologies, Inc., Seattle, WA (US)

( * ) Notice: Subject to any disclaimer, the term of this patent is extended or adjusted under 35 U.S.C. 154(b) by 184 days.

(21) Appl. No.: 17/847,962

(22) Filed: Jun. 23, 2022

(51) Int. Cl.
  *G06F 1/00* (2006.01)
  *A61B 5/00* (2006.01)
  *G06F 1/3231* (2019.01)
  *G06N 5/022* (2023.01)

(52) U.S. Cl.
  CPC .......... *G06F 1/3231* (2013.01); *A61B 5/6844* (2013.01); *G06N 5/022* (2013.01)

(58) Field of Classification Search
  CPC .............................. G06F 1/3231; G06N 5/022
  See application file for complete search history.

(56) References Cited

U.S. PATENT DOCUMENTS

| | | | | |
|---|---|---|---|---|
| 10,152,162 | B1* | 12/2018 | Bokma | G06F 3/04186 |
| 11,256,941 | B2* | 2/2022 | Hwang | H04M 1/725 |
| 11,857,298 | B1* | 1/2024 | Allec | G04B 47/063 |
| 2014/0354567 | A1* | 12/2014 | Park | G06F 3/0488 |
| | | | | 345/173 |
| 2019/0069848 | A1* | 3/2019 | Clavelle | A61B 5/6824 |
| 2020/0143027 | A1* | 5/2020 | Toumazou | G06F 1/163 |
| 2021/0192249 | A1* | 6/2021 | Hwang | G06V 40/67 |
| 2023/0305630 | A1* | 9/2023 | Shin | G06F 3/017 |

* cited by examiner

*Primary Examiner* — Mohammed H Rehman
(74) *Attorney, Agent, or Firm* — Athorus, PLLC (57) ABSTRACT

Described are systems, methods, and apparatus that utilize multiple sensors to conserve battery life of a device, limit potential disruption to a user, and reliably detect whether the device is worn by the user. In one example, a first sensor, such as an infrared sensor, may be activated to determine a proximity of the device to an object. If the device is within a proximity of the object, a second sensor, such as a photoplethysmography (PPG) sensor, may be activated to verify that the device is being worn by the user and then to continue collecting data that may be used to determine biometrics for the user.

20 Claims, 9 Drawing Sheets

WEARABLE DEVICE BODY DETECTION

BACKGROUND

Wearable devices to monitor user biometrics, such as skin temperature, heartrate, etc., have become prevalent in use. Accuracy of those devices has become more important, as has battery conservation. Of particular importance to both accuracy and battery conservation is accurately determining when the device is worn or within a proximity of a user such that biometric data can be determined, and when the device is not worn or within a proximity of the user, such that biometric data can be determined. A failure to accurately detect the status of the device at any point will result in degraded user experience, such as missing biometric data, and lost battery life. Increasing the difficulty of this problem is that accurately detecting the status of the device is more difficult for some skin tones.

Traditional techniques utilize data collected by photoplethysmography ("PPG") sensors on a device. However, these sensors often provide inaccurate data, especially for darker skin-tone users. Likewise, when the sensors are active, such as green light emitting diode ("LED") sensors, and the device is not worn by the user, the visibility of the light emitted by the sensor(s) may be disruptive to the user.

BRIEF DESCRIPTION OF DRAWINGS

The detailed description is described with reference to the accompanying figures.

DETAILED DESCRIPTION

Described is a system, method, and apparatus that optimizes the use of sensors on a wearable device based on whether the wearable device is in a state to collect sensor data to generate biometric data for a user or if the device is in a state in which some or all of the sensors should be disabled. As discussed further below, different types of sensors may be utilized to determine when to change a state of the wearable device. For example, if the device is in a state in which it cannot collect sensor data that may be used to generate biometric data for a user, referred to herein as "off-body," some or all of the sensors may be deactivated to conserve battery power and to avoid potential disruption to a user as a result of visible light being emitted from sensors of the device. In comparison, if the wearable device is in a position or state in which it can collect sensor data that may be used to generate biometric data for a user, referred to herein as "on-body," some or all of the sensors may be activated to collect sensor data that is used to generate the biometric data about the user.

For ease of explanation and discussion herein, the different positions of the device will be generally referred to herein as on-body or off-body. As will be appreciated, on-body refers to any position in which the wearable device is in contact or within a defined proximity of an animate object, such as a human. In comparison, off-body refers to any position in which the wearable device is not within the defined proximity of the body.

As discussed further herein, the device may change states or transition between on-body and off-body based on different events. For example, if, while the wearable device is off-body, a movement of the wearable device is detected, a first sensor, such as an infrared sensor ("IR sensor") may be activated to collect first proximity data to determine whether the device is within a defined proximity of an object, such as the user. If it is determined that the proximity of the device is not within the defined proximity, the first sensor may be deactivated, thereby conserving power and the wearable device may stay in the off-body state. However, if it is determined that the device is within a defined proximity of the user, a second sensor, such as a visible light photoplethysmography ("PPG") sensor on the wearable device may be activated to verify that the device is within a defined proximity of an animate object, such as the user, transition the device to an on-body state, and begin collecting second sensor data that may be used to generate biometric data about the user.

As discussed further below, and as is known in the art, visible light PPG sensors, such as visible sensors operating in the 530 nanometer wavelength (green), a 645 nanometer wavelength (red), or a 470 nanometer wavelength (blue) often have difficulty collecting biometric data for darker skin-tone users. In comparison, IR sensors, while requiring higher power requirements and thus battery consumption, are highly accurate at determining if the device is within a proximity of an object. Accordingly, as discussed herein, the IR PPG sensor and the visible light PPG sensors may be periodically or continually used to either collect biometric data or verify that a detected object is an animate object (e.g., user), in the case of the visible light PPG sensors, to detect proximity data, in the case of the IR PPG sensors, or both, thereby balancing a tradeoff between accuracy and power consumption.

For ease of explanation, each of the different visible light sensors and/or IR sensors are referred to herein as individual sensors. However, it will be understood that a single sensor component may be utilized that includes different light emitting diodes ("LED") for the different wavelengths and one or more photodiodes may be used to receive the reflections of the different transmitted wavelengths. Accordingly, reference to activating, deactivating, or otherwise controlling different sensors includes both activating, deactivating, or otherwise controlling independent sensors and/or activating, deactivating, or otherwise controlling different LEDs of a single sensor component. For example, disabling a visible light sensor and enabling an IR sensor, as discussed herein, includes both/either disabling the visible LED(s) and enabling the IR LED(s) of a single sensor component and/or disabling one or more individual (or combined) visible light sensors and enabling a separate IR sensor.

Figure 1:
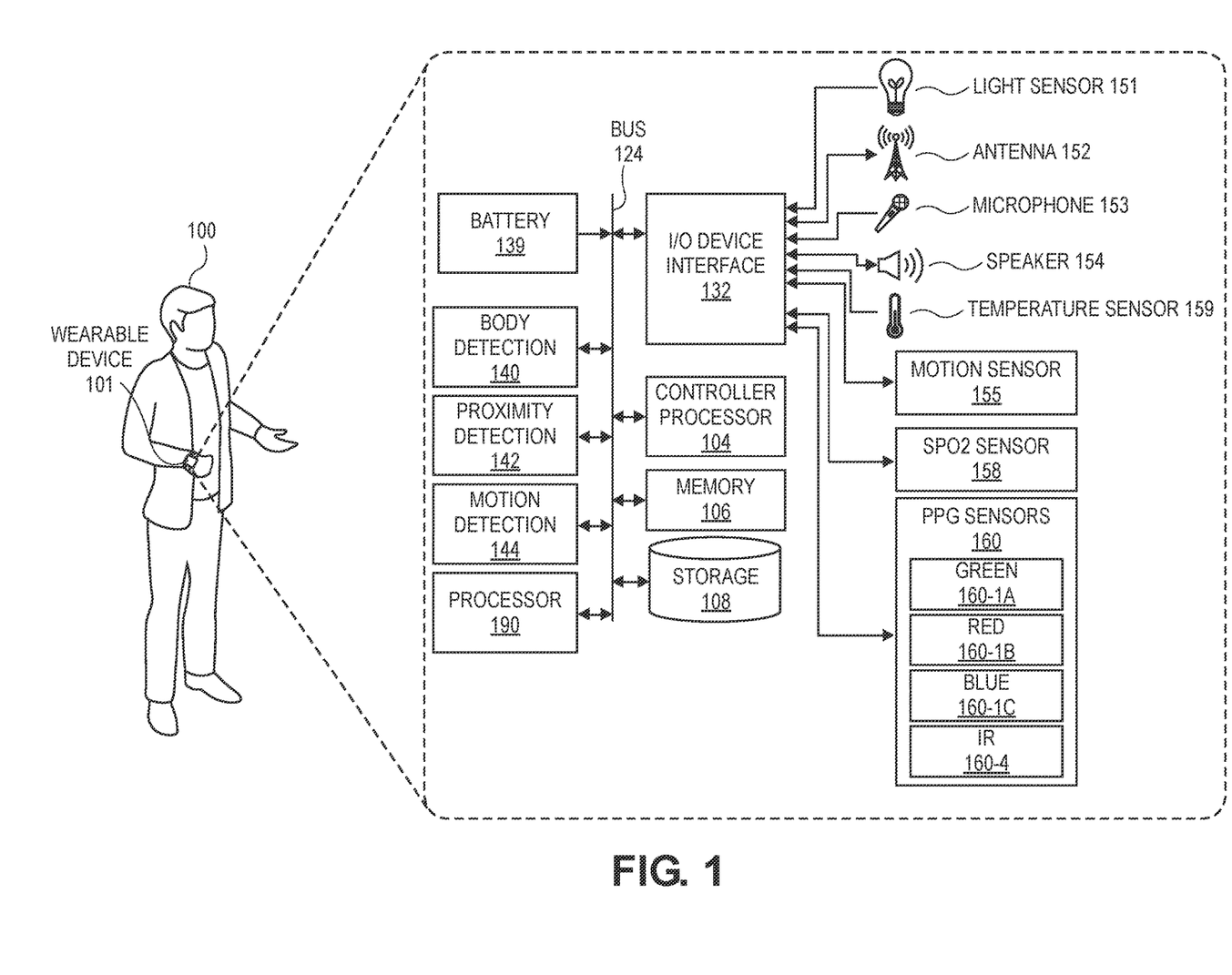
FIG. 1 is an example diagram of a wearable device apparatus, in accordance with described implementations.

FIG. 1 is an example diagram of a wearable device apparatus 101 that may be worn by a user 100, in accordance with described implementations.

The wearable device apparatus 101 may be any form of wearable device. For example, the wearable device apparatus may be in the form of a wristband, a necklace, headphones, a ring, a watch, an earring, a headband, glasses, an article of clothing, an on-skin apparatus (e.g., an adhesive patch), an implant, etc.

In operation, the wearable device 101 may include a battery 139 and/or other power source, computer-readable and computer-executable instructions, one or more sensor/state processors 190 that may include a central processing unit (CPU) 104 for processing sensor data, computer-readable instructions, etc., and a memory 106 for storing data and instructions of the wearable device apparatus. The memory 106 may individually include volatile random-access memory (RAM), non-volatile read only memory (ROM), non-volatile magnetoresistive random-access memory (MRAM) and/or other types of memory. The wearable device 101 may also include a data storage component 108 for storing data, controller/processor-executable instructions, machine learning models, etc. Each data storage component may individually include one or more non-volatile storage types such as magnetic storage, optical storage, solid-state storage, etc.

Computer instructions for operating the wearable device 101 and its various components may be executed by the controller(s)/processor(s) 104, using the memory 106 as temporary "working" storage at runtime. A wearable device's 101 computer instructions may be stored in a non-transitory manner in non-volatile memory 106, storage 108, or an external device(s). Alternatively, some or all of the executable instructions may be embedded in hardware or firmware on the wearable device 101 in addition to, or instead of software.

For example, and as discussed further below, the wearable device 101 may include computer instructions that, when executed by the one or more processors 104/190 of the wearable device, perform body detection 140 to determine if the device is on-body or off-body, computer instructions that, when executed by the one or more processors of the wearable device, perform proximity detection 142 to determine if the device is within a defined proximity of an object, such as a body, and/or computer instructions, that when executed by the one or more processors of the wearable device, perform motion detection 144 to determine if the wearable device has been moved.

The wearable device 101 also includes an input/output device interface 132. A variety of components may be connected through the input/output device interface 132. Additionally, the wearable device 101 may include an address/data bus 124 for conveying data among components of the wearable device. Each component within the wearable device 101 may also be directly connected to other components in addition to (or instead of) being connected to other components across the bus 124.

The wearable device 101 may be "headless" and may primarily rely on spoken commands for input and/or through interaction with one or more control interfaces or buttons. In other examples, the wearable device 101 may include a display, which may allow a touch-based interface. The wearable device 101 may also include input/output device interfaces 132 that connect to a variety of components such as an audio output component, such as a speaker 154. The wearable device 101 may also include an audio capture component. The audio capture component may be, for example, a microphone 153 or array of microphones, etc. The microphone 153 may be configured to capture audio, such as environmental noises, voices, speech, etc.

The wearable device 101 may also include other sensors that collect sensor data that may be representative of user data and/or the environment in which the user is located. Any number and/or type of sensors may be included in the device. In the illustrated example, in addition to the microphone, the wearable device 101 may include a light sensor 151 that may measure the ambient light, one or more temperature sensors 159 that may measure the ambient temperature and/or measure the temperature of the user when wearing the wearable device, a motion sensor 155, such as an accelerometer, gyroscope, etc., to measure movement of the user, an oxygen saturation sensor ("SpO2") 158 to measure the saturation percentage of oxygen in the blood, one or more photoplethysmogram ("PPG") sensors 160, such as an IR sensor 160-4, a visible light green sensor 160-1A, a visible light red sensor 160-1B, and/or a visible light blue sensor 160-1C. Other sensors and/or monitors may likewise be included on the wearable device 101.

The wearable device 101 may also include a communication interface, such as an antenna 152 to enable wireless communication 103 between the wearable device 101 and another device, such as a portable device. Any form of wireless communication may be utilized to facilitate communication from/to the wearable device 101. For example, any one or more of ZIGBEE, WI-FI, WiMAX, BLUETOOTH, Z-WAVE, NFC, cellular, etc., may be used to communicate to/from the wireless device 101.

Figure 2:
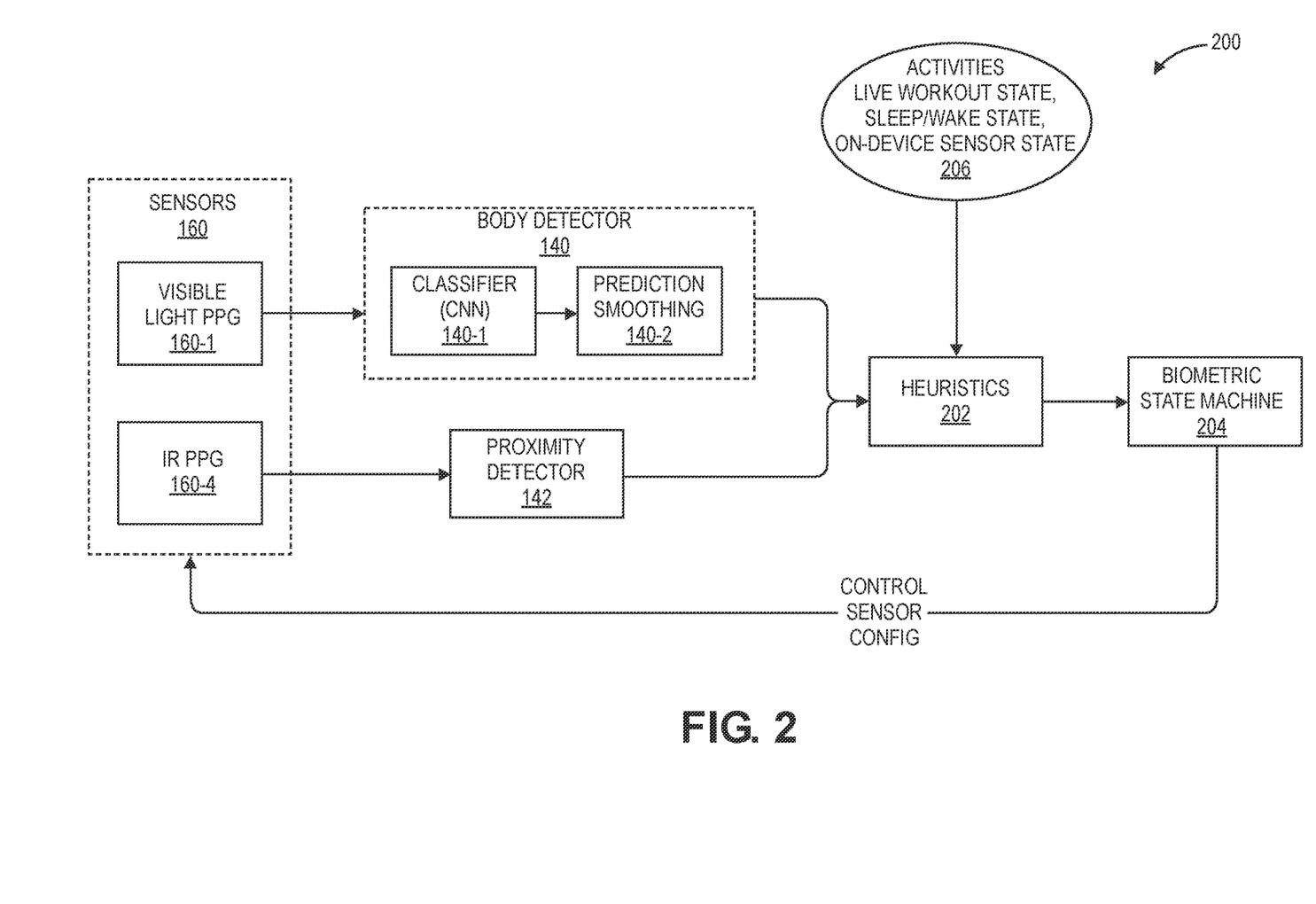
FIG. 2 is a block diagram of an example body detection architecture of a wearable device, in accordance with described implementations.

FIG. 2 is a block diagram of an example body detection architecture 200 of a wearable device, such as the wearable device 101 (FIG. 1) that is operable to determine whether the wearable device is on-body or off-body, in accordance with described implementations.

As discussed above, the architecture 200 may include a plurality of PPG sensors 160, such as one or more visible light PPG sensors 160-1 and one or more IR PPG sensors 160-4. Depending on the state of the wearable device and/or events detected by the wearable device, some, all, or none of the sensors may be active. For example, when the wearable device is off-body, all of the PPG sensors 160 may be inactive. As another example, when movement of the device is detected, referred to herein as an event, the IR PPG sensors 160-4 may be activated, without activating the visible light PPG sensor(s) 160-1 and the sensor data from the IR PPG sensor 160-4 utilized by a proximity detector 142 to determine if the wearable device is within a defined proximity of an object. Proximity detection is discussed in further detail below with respect to FIGS. 4A and 4B.

In comparison to utilizing the IR PPG sensor(s) 160-4 to determine the proximity of the wearable device to an object, the visible light PPG sensor(s) 160-1 may be utilized to confirm or verify that the object is an animate object, referred to herein as a body. An animate object may be any living object, such as a human or other animal, mammal, etc.

As discussed further below; sensor data from the visible light PPG sensor(s) 160-1 may be utilized by a machine learning model 140-1, such as a convolutional neural network ("CNN"), to generate a prediction or classification as to whether the wearable device is on-body or off-body. The prediction output from the machine learning model 140-1 may then be filtered or smoothed, referred to herein as prediction smoothing 140-2, based on, for example, prior states of the wearable device so that the state of the wearable device does not rapidly change or oscillate between on-body and off-body. The machine learning model 140-1 and the prediction smoothing 140-2 collectively operate as a body detector 140 that provides an output as to whether the wearable device is on-body or off-body. Additional details for determining whether the device is on-body or off-body are discussed further below with respect to FIG. 5.

Still further, in some implementations, the on-body/off-body prediction output from the body detector 140 and/or the proximity output from the proximity detector 142 may be provided to a heuristics filter 202 that considers inputs from the body detector 140, the proximity detector 142, as well as other inputs 206, such as activities in which it has been determined that the user is involved. For example, the wearable device 101 may determine or be informed by the user 100 that the user is participating in an activity. Activities include, but are not limited to, workouts performed by the user, sleep/wake states, etc.

The heuristics filter 202, considering all the received inputs 206, provide an output indicating a state or state transition of the wearable device that is provided to a biometric state machine 204 of the wearable device and used to drive the biometric state machine 204 and control the device sensors 160.

As discussed below, the biometric state machine 204, based on the received output from the heuristics filter 202, controls the state and configuration of the sensors 160, such as the visible light sensors 160-1, IR sensors 160-4, a motion sensor 155 (FIG. 1), etc., and may transition the wearable device and/or sensors 160 between different states in which sensor data is used to generate biometric data or not used to generate biometric data (e.g., if the sensor is inactive or the device is off-body).

Figure 3A:
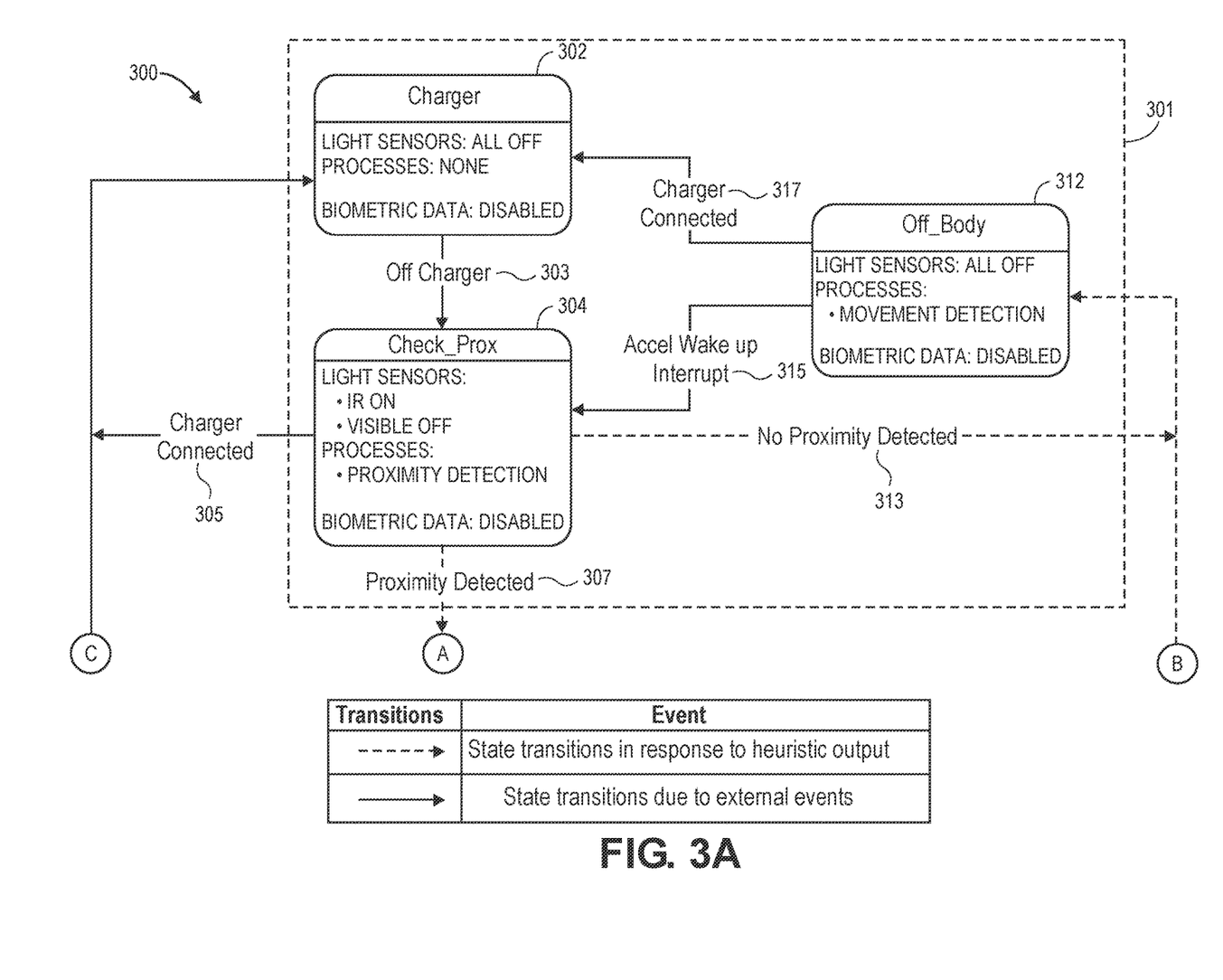
FIGS. 3A through 3B is an example state diagram indicating the different states of the wearable device, the transitions between those states, and the activity of the sensors of the wearable device while in those states, in accordance with described implementations.
Figure 3B:
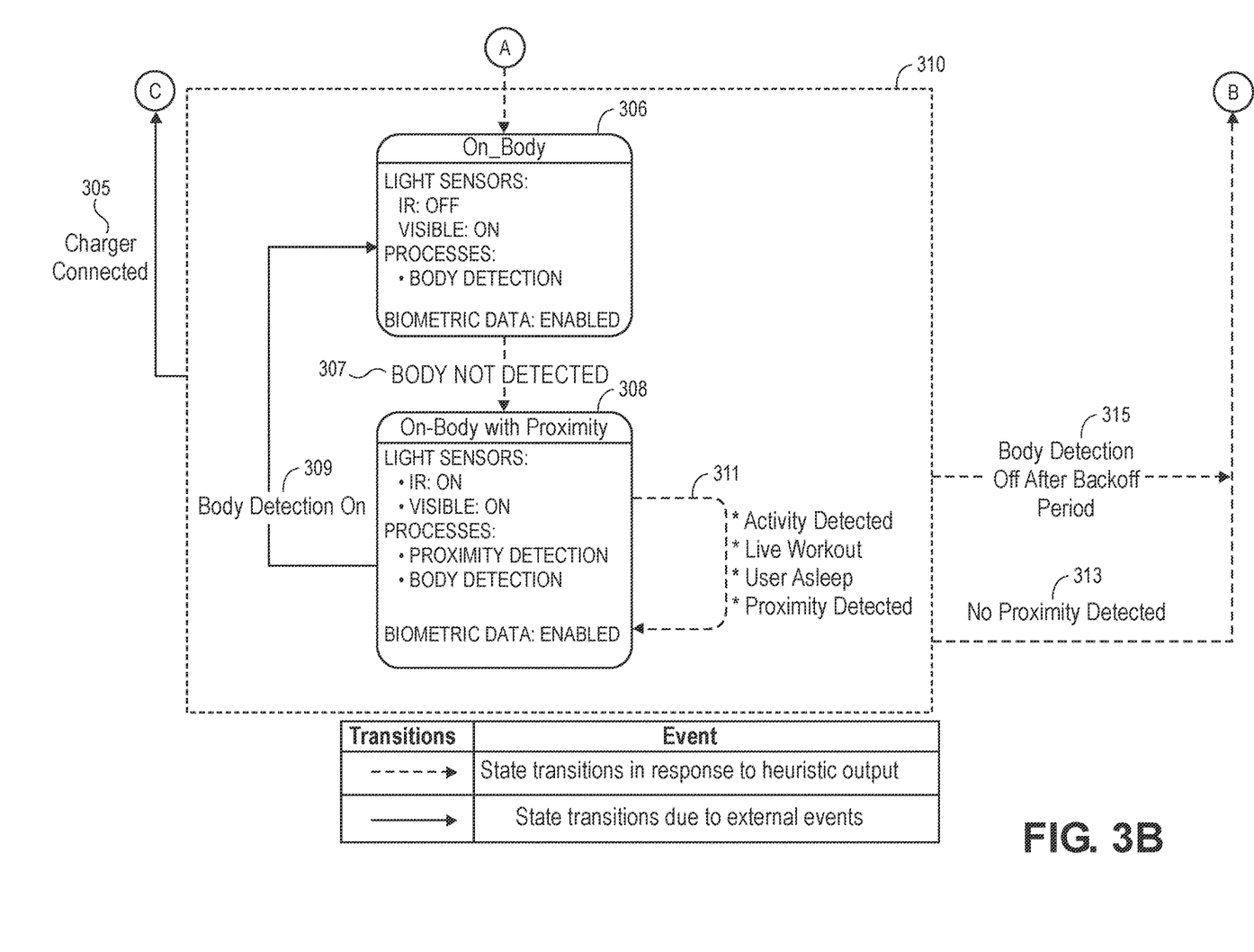

FIGS. 3A through 3B is an example state diagram 300 indicating the different states of the wearable device, the transitions between those states, and the activity of the sensors of the wearable device while in those states, in accordance with described implementations.

Referring first to the off-body state 312, when the device is determined to be off-body, all visible light and IR sensors, and any other light emitting diodes ("LEDs") are in an inactive state, biometric data collection is disabled, and the device is overall in a low power state, thereby conserving power and eliminating the chance of emitting visible light that might be disruptive to a user while the wearable device is off-body. In addition, a movement detection process, discussed further below with respect to FIG. 6, and corresponding motion sensor, may be active such that data from the motion sensor 155 is monitored and processed to determine if the device has been moved. Likewise, the power source or charger input may be monitored to determine if the device has been connected to power or is otherwise receiving a charge to the battery of the wearable device.

In some implementations, if it is determined that the device has been connected to power or is otherwise receiving a charge, as indicated by the charger connected line 317, the device may transition to a charger state 302 in which all of the sensors are deactivated, all of the processes are deactivated, and biometric data collection is disabled. Such a state may exist when the wearable device is generally removed during charging. In other implementations in which the device may be charged while on-body, the charger state 302 may be omitted and transition between states in response to detecting a charge of the device may likewise be omitted.

If, while the device in the off-body state 312, it is determined by the movement detection process that the device has been moved, a wakeup interrupt event 315 is generated and the device transitions from the off-body state to a check proximity state 304. Likewise, if the device is in a charger state 302 and it is determined that the charge to the device is disconnected or otherwise removed, as indicated by line 303, the device may transition into the check proximity state 304.

As illustrated in FIG. 3A, when the device is in the check-proximity state 304, the IR sensor is activated to collect IR sensor data, while the visible light sensors remain deactivated. As discussed further below with respect to FIGS. 4A and 4B, the collected IR sensor data is processed to determine if the device is within a defined proximity of an object, such as an animate object (e.g., a user). While in the check-proximity state 304, collection of biometric data remains disabled and the visible light sensors remain disabled to conserve battery power and to avoid emitting visible light that may be disruptive to the user if it is determined that the device is not within a defined proximity of an object—e.g., remains off-body. For example, a device may transition to the check-proximity state 304 even though it is not worn by a user in response to the device being disconnected from the charger or if the device is moved, bumped, or if a table or other surface upon which the device is resting is moved or bumped. Overall, when the device is in the off-body state 312, the charger state 302, or check proximity state 304, the device is considered to be in an off-body position, the visible light sensors disabled, and the biometric data not collected.

If it is determined, while in the check proximity state 304 that the charger is connected, the device may transition back to the charger state 302. As noted above, in other implementations, the charger state 302 and monitoring for charger connection may be omitted for devices that may be charged while on-body. Likewise, if it is determined, while the device is in the check proximity state 304, that the device is not within a defined proximity of an object, as illustrated by dashed line 313, the device may transition back to the off-body state 312, the IR sensor disabled, and movement detection may be resumed. However, if it is determined by the proximity detection process that the wearable device is within a defined proximity of an object, such as the user, the wearable device transitions from the check proximity state 304 to the on-body state 306, as illustrated by dashed line 307.

Figure 5:
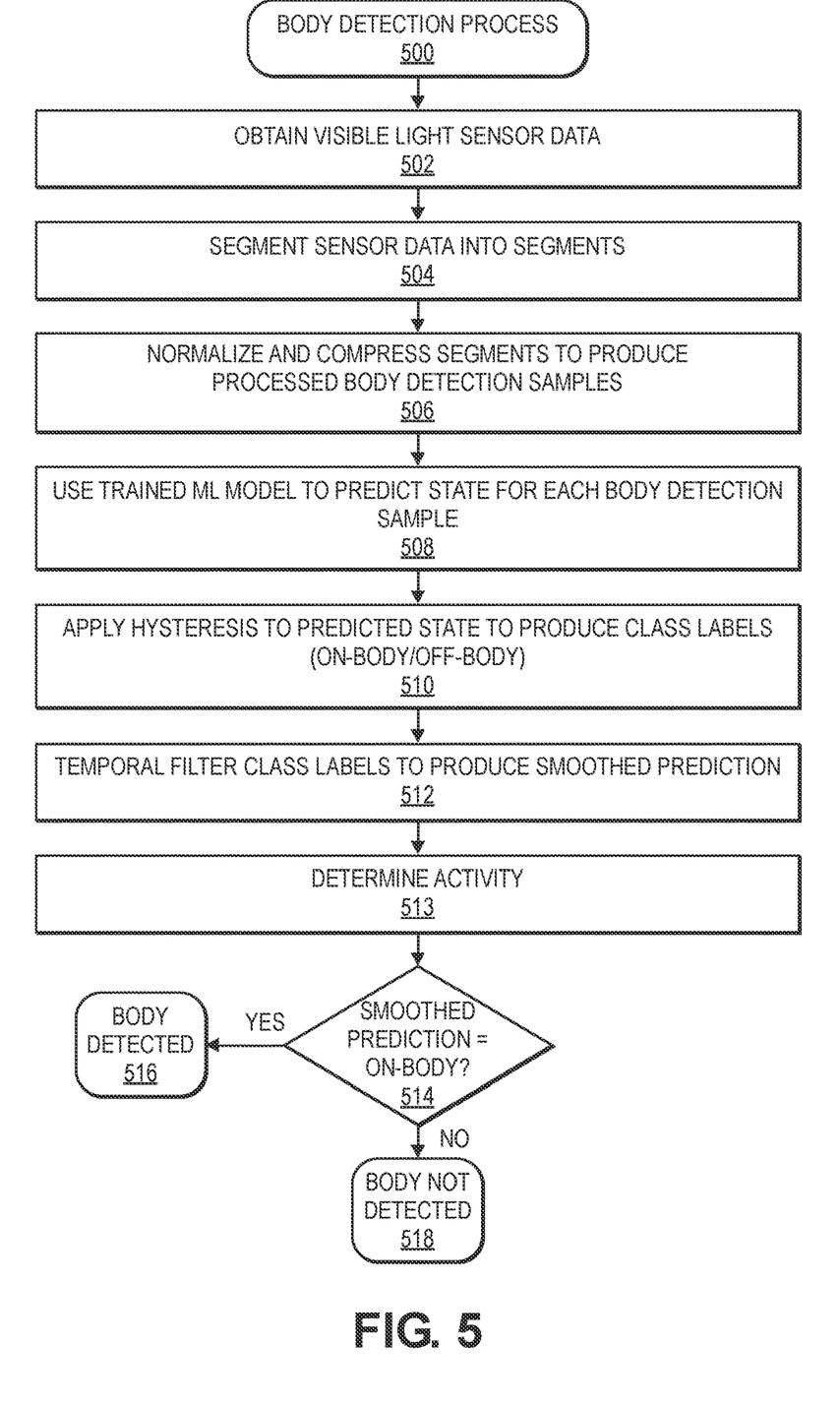
FIG. 5 is an example body detection process, in accordance with described implementations.

Referring now to FIG. 3B, when the device is in the on-body state 306, the visible light sensors are activated and, in some implementations, the IR sensor(s) are deactivated. In addition, the body detection process, discussed further below with respect to FIG. 5, is activated which utilizes visible light sensor data to verify that the detected body is an animate body, such as the user, and that biometric data can be determined from the collected visible light sensor data. In addition to verifying that the detected object is an animate object, biometric data collection is also enabled. As long as the device remains in the on-body state 306 and the body detection process determines that the device is on-body, the IR sensor may remain deactivated, thereby conserving battery power of the wearable device. However, if the body detection process determines that the body is not detected, the wearable device transitions to the on-body with proximity state 308, as illustrated by line 307.

In the on-body with proximity state 308, both the visible light sensor(s) and the IR sensor(s) are active and both the body detection process, which utilizes visible light sensor data, and the proximity detection process, which utilizes IR sensor data, are active and process received sensor data to determine if the wearable device is still within a proximity of an object and able to collect visible light data that is usable to determine that the object is an animate object and/or generate biometric data about the user. In addition, other events or activities may be monitored/detected and utilized as inputs to determine if the wearable device is on-body or off-body, as illustrated by dashed line 311. Other events or activities include, but are not limited to, movement of the device, whether the user has been determined or indicated that they are exercising (live workout), whether the user is determined to be asleep, whether the user is determined to be awake, etc. While the device is in the on-body with proximity state 308, biometric data may continue to be collected.

As indicated by the dashed line/square 310, the on-body state 306 and the on-body with proximity state 308, the device is maintained in an overall on-body state such that biometric data continues to be collected. If, while the device is in either the on-body state 306 or the on-body with proximity state 308, it is determined that the device has been connected to a charger, as indicated by line 305, in some implementations, the device may transition to the charger state 302 and all sensors and data collection may be disabled. In other implementations, charger connection monitoring and the charger state 302 may be omitted and state transition may not occur when the device is connected to a charger, thereby enabling continuous use of the wearable device while charging.

If it is determined in the on-body with proximity state 308 that the device is still on-body, as illustrated by line 309, the device transitions back to the on-body state 306 and the IR sensor(s) are disabled, thereby conserving power. However, if it is determined by the proximity process that the wearable device is no longer within a defined proximity of an object, as illustrated by line 313, the wearable device may transition to the off-body state 312 and the visible light sensor(s) and IR sensor(s) maybe be disabled. Likewise, after a backoff period, which may be based on an activity determined for the user, if it is still determined that the device is off-body, even if the device is within a proximity of an object, the wearable device may transition from the on-body state 306 or the on-body with proximity state 308 back to the off-body state 312, as indicated by line 315. Backoff periods and on-body to off-body determinations by the body detection process are discussed further below with respect to FIG. 5. Overall, when the wearable device is in the on-body state 306 and on-body with proximity state 308, the wearable device is considered to be in an on-body position, the visible light sensors enabled, and biometric data collected.

Figure 4A:
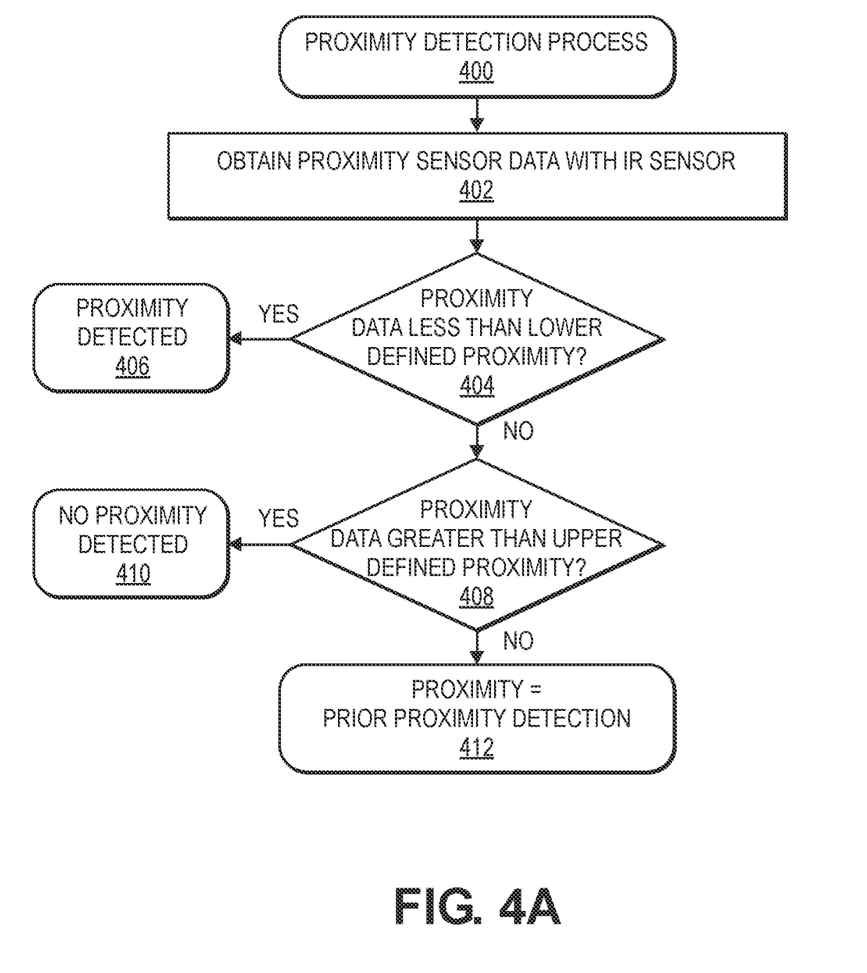
FIG. 4A is an example proximity detection process, in accordance with described implementations.

FIG. 4A is an example proximity detection process 400, in accordance with described implementations. The example process 400 may be performed when a wearable device transitions into the check proximity state 304 (FIG. 3A) or into the on-body with proximity state 308 (FIG. 3B).

The example process 400 begins by receiving proximity sensor data from the IR sensor(s) of the wearable device, as in 402. As is known, proximity determination through IR sensors utilize a reflective indirect incidence principle. In particular, a photodiode receives the radiation emitted by an IR LED once reflected back by an object. The closer the object to the IR LED/photodiode, the higher the intensity of the incident radiation on the photodiode. The intensity may then be converted to voltage to determine distance between the photodiode and the object that reflected the IR light. Determining proximity between an IR LED and photodiode and an object is known in the art and need not be discussed in detail herein.

A determination may then be made as to whether the proximity data is less than a lower defined proximity, as in 404. The lower defined proximity may be any defined value and may vary for different users, different wearable devices, different wearable device types, etc. In general, the lower defined proximity may be a value that, if the proximity data is below that value, it may be determined to be within a defined proximity of an object. In some implementations, the lower defined proximity may be a distance value, such as five millimeters. In another example, the lower defined proximity may be an intensity value for the proximity data. In still another example, the proximity data may be monitored over a period of time, such as one second intervals, and a confidence score generated indicating a confidence as to whether the device is within a proximity of an object. For example, if the proximity data varies greatly over the period of time, it may be assigned a low confidence score. In comparison, if the proximity data consistently has a high intensity (indicative of the sensor being close to an object), it may receive a high proximity score. In such an example, the lower defined proximity may be indicative of a confidence score. In other implementations, the lower defined proximity may be larger or smaller.

If it is determined that the proximity data is less than the lower defined proximity, the example process 400 may determine that proximity of the device to an object is detected—i.e., the wearable device is within a defined proximity to an object, as in 406.

If it is determined that the proximity data is not less than the lower defined proximity, a determination is made as to whether the proximity data is greater than an upper defined proximity, as in 408. Like the lower defined proximity, the upper defined proximity may be any value and may be different for different users, different wearable devices, different wearable device types, etc. The only requirement is that the upper defined proximity must be larger than the lower defined proximity.

If it is determined that the proximity data is greater than the upper defined proximity, the example process 400 may determine that the device is not within a proximity of an object—i.e., the wearable device is not within a defined proximity of an object, as in 410. However, if it is determined that the proximity data is not greater than the upper defined proximity, the example process 400 may determine that the proximity of the wearable device is to remain the same as the proximity that was previously determined for the device by the example process 400 at a prior point in time, as in 412. For example, if, at the current time (x) at which the example process 400 is performed it is determined that the proximity data is not greater than the upper defined proximity, the example process may determine the proximity of the wearable device is to remain the same as it was at a prior time (x-1).

Utilizing a lower defined proximity and an upper defined proximity such that there are three potential determinations from the example process 400 prevents quick successive changes in the proximity output prediction of the example process. Overall, the three outcomes discussed above with respect to the example process follow the below structure at each point in time in which the example process 400 is performed:

$$x(t) = \begin{cases} \text{Proximity} & \text{if } x(t) < \text{Lower Proximity} \\ x(t-1) & \text{if Lower Proximity} < x < \text{Upper Proximity} \\ \text{No Proximity} & \text{if } x > \text{Upper Proximity} \end{cases}$$

Figure 4B:
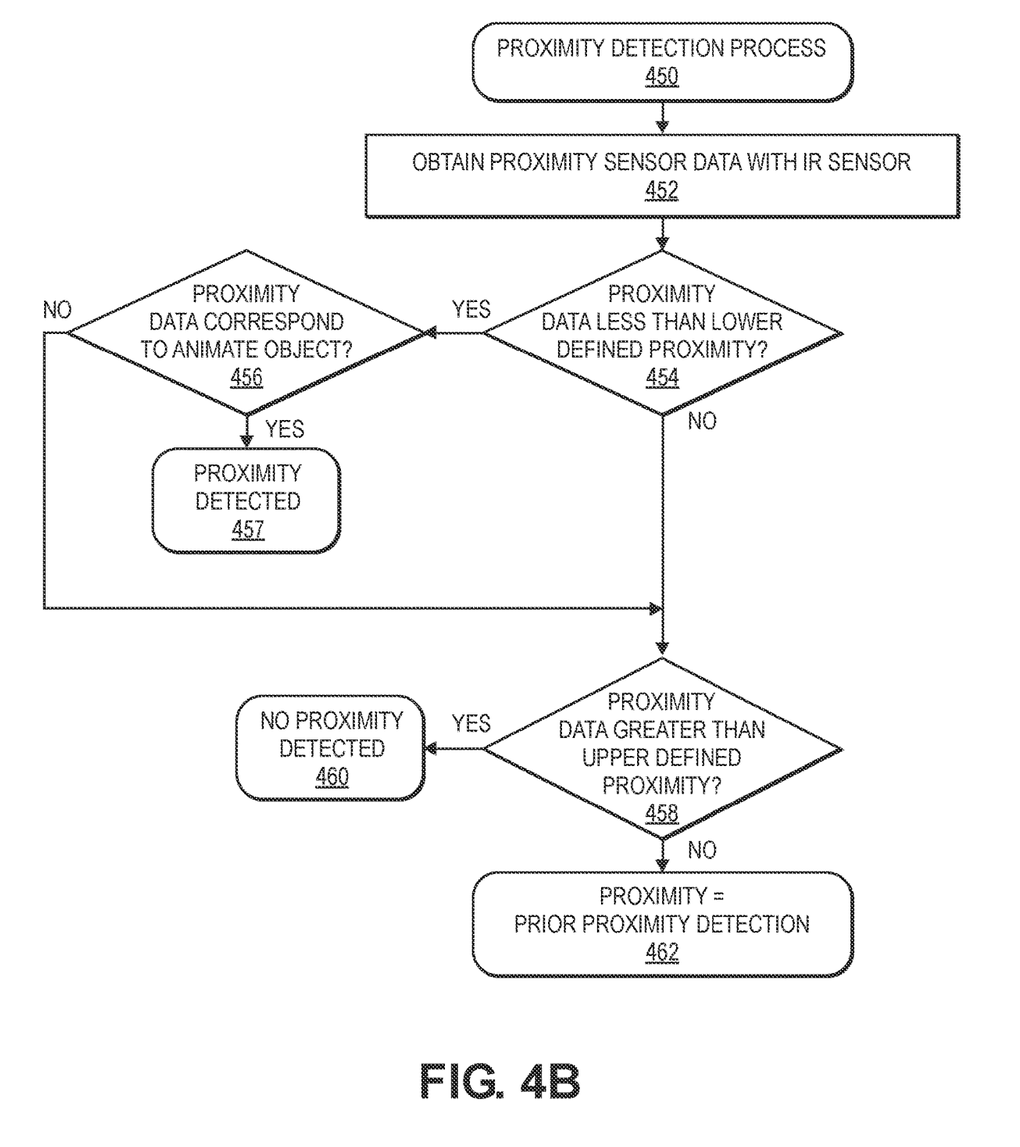
FIG. 4B is another example proximity detection process, in accordance with described implementations.

FIG. 4B is another example proximity detection process, in accordance with described implementations. In comparison to the example process 400 (FIG. 4A) in FIG. 4B an additional assessment from the IR data to initially determine if the object is an animate object may be considered in determining if the wearable device is within a defined proximity of an object.

The example process 450 may be performed when a wearable device transitions into the check proximity state 304 (FIG. 3A) or into the on-body with proximity state 308 (FIG. 3B).

The example process 450 begins by receiving proximity sensor data from the IR sensor(s) of the wearable device, as in 452. As is known, proximity determination through IR sensors utilize a reflective indirect incidence principle. In particular, a photodiode receives the radiation emitted by an IR LED once reflected back by an object. The closer the object to the IR LED/photodiode, the higher the intensity of the incident radiation on the photodiode. The intensity may then be converted to voltage to determine distance between the photodiode and the object that reflected the IR light. Determining proximity between an IR LED and photodiode and an object is known in the art and need not be discussed in detail herein.

A determination may then be made as to whether the proximity data is less than a lower defined proximity, as in 454. The lower defined proximity may be any defined value and may vary for different users, different wearable devices, different wearable device types, etc. In general, the lower defined proximity may be a value that, if the proximity data is below that value, it may be determined to be within a defined proximity of an object. In some implementations, the lower defined proximity may be a distance value, such as five millimeters. In another example, the lower defined proximity may be an intensity value for the proximity data. In another example, the lower defined proximity may be an intensity value for the proximity data. In still another example, the proximity data may be monitored over a period of time, such as one second intervals, and a confidence score generated indicating a confidence as to whether the device is within a proximity of an object. For example, if the proximity data varies greatly over the period of time, it may be assigned a low confidence score. In comparison, if the proximity data consistently has a high intensity (indicative of the sensor being close to an object), it may receive a high proximity score. In such an example, the lower defined proximity may be indicative of a confidence score. In other implementations, the lower defined proximity may be larger or smaller.

If it is determined that the proximity data is less than the lower defined proximity, a determination may be made as to whether the proximity data corresponds to an animate object, as in 456. For example, the proximity data may be processed by a trained machine learning model to determine if the proximity data is indicative of a heart rate, respiratory rate, or other biometric that is indicative of an animate object. If it is determined that the proximity data corresponds to an animate object, the example process 450 may determine that proximity of the device to an object is detected—i.e., the wearable device is within a defined proximity to an object, as in 457. By considering whether the object is an animate object when determining proximity, an initial assessment may be made as to whether the device is on-body or whether the detected object is another type of object, such as a table surface, floor, etc. Such initial detection may further increase accuracy of state determination and also further decrease any chance of visible light sensors being activated when the wearable device is off-body.

If it is determined that the object is not an animate object, or if it is determined that the proximity data is not less than the lower defined proximity, a determination is made as to whether the proximity data is greater than a upper defined proximity, as in 458. Like the lower defined proximity, the upper defined proximity may be any value and may be different for different users, different wearable devices, different wearable device types, etc. The only requirement is that the upper defined proximity must be larger than the lower defined proximity.

If it is determined that the proximity data is greater than the upper defined proximity, the example process 450 may determine that the device is not within a proximity of an object—i.e., the wearable device is not within a defined proximity of an object, as in 460. However, if it is determined that the proximity data is not greater than the upper defined proximity, the example process 450 may determine that the proximity of the wearable device is to remain the same as the proximity that was previously determined for the device by the example process 450 at a prior point in time, as in 462. For example, if, at the current time (x) at which the example process 450 is performed and it is determined that the proximity data is not greater than the upper defined proximity, the example process may determine the proximity of the wearable device is to remain the same as it was at a prior time (x-1).

Utilizing a lower defined proximity and an upper defined proximity such that there are three potential determinations from the example process 450 prevents quickly successive changes in the proximity output prediction of the example process. Overall, the three outcomes discussed above with respect to the example process follow the below structure at each point in time in which the example process 450 is performed:

$$x(t) = \begin{cases} \text{Proximity} & \text{if } x(t) < \text{Lower Proximity} \\ x(t-1) & \text{if Lower Proximity} < x < \text{Upper Proximity} \\ \text{No Proximity} & \text{if } x > \text{Upper Proximity} \end{cases}$$

FIG. 5 is an example body detection process 500, in accordance with described implementations. The example process 500 may be performed any time the device is in the on-body state 306 or in the on-body with proximity state 308. The example process may be continually or periodically performed while in either state 306/308 to continually or periodically confirm that the wearable device is still on-body.

The example process 500 begins by receiving visible light sensor data from one or more visible light sensors of the wearable device 500, as in 502. In some implementations, the received visible light sensor data may then be segmented, as in 504. For example, in some implementations, the duration of the sensor data may be segmented into overlapping five-second segments. In other implementations, the segments may have shorter or longer durations and may overlap or not overlap.

The segments may then be normalized and compressed to produce a processed body detection sample for each segment, as in 506. For example, each segment may be filtered and normalized by removing the mean and scaling to unit variance. Additionally, in some implementations, compression of each segment may be performed through a non-linear transformation of the segment to further compress the signal range of the segment. Such compression may be done to enable quantized fixed-point model inference on the wearable device, thereby reducing compute time and reducing memory requirements.

Each processed body detection sample may then be provided to a trained machine learning model, such as a CNN, that outputs, for each processed body detection sample, a prediction as to whether the device is on-body or off-body, as in 508. In some implementations, the output may be a floating point between zero and one, with zero corresponding to off-body and one corresponding to on-body. The prediction may be indicative of a probability that the input processed body detection sample is on-body or off-body. In other implementations, the output may be binary or correspond to a different range of values or indications.

A hysteresis may also be applied to each probability output by the machine learning model to produce a class label for each segment, as in 510. For example, the predicted output for each segment by the machine learning model may be assigned a class label of either on-body or off-body. For example, if the probability output is between 0) and 0.50, the hysteresis may assign a class label of off-body to the segment. In comparison, if the probability output is above 0.50, the hysteresis may assign a class label of on-body to the segment. In other implementations, the hysteresis ranges/values may be different. In some implementations, the hysteresis ranges may change to bias the overall probability based on historical probabilities and the probabilities of the segments of the data sample, thereby limiting frequent changes in device state between on-body and off-body. For example, if a prior segment was determined to be on-body, the hysteresis may require a lower probability, e.g., between 0.0 and 0.25, before a class label of off-body is assigned. Likewise, if a prior segment was determined to be off-body, the hysteresis may require a higher probability, e.g., above 0.75, before a class label of on-body is assigned to the segment. The class label is an overall indication for each segment as to whether the wearable device is determined to be on-body or off-body.

Still further, in some implementations, the class labels for a data sample or group of segments may also be temporal filtered to produce a smoothed prediction, as in 512. For example, temporal filtering may smooth out the predictions to remove oscillations between class labels. For example, if a series of ten class labels include eight on-body class labels and two off-body class labels, temporal filtering may adjust the class labels during that period to all be indicated as on-body, thereby eliminating oscillation between states.

In addition to predicting whether the device is predicted to be on-body or off-body, any activities of the user may also be determined, as in 513. For example, based on biometric data and/or input from the user, an activity of the user may be determined. Activity determination may be from a prior point in time and considered on-going during the period of time in which the visible light sensor data was obtained by the example process 500. Activities may include, but are not limited to, sleep, awake, exercising, etc.

Based on the activity data, a backoff period may be assigned that requires a defined series of samples, segments, or period of time in which the assigned class labels have changed before the example process 500 returns a change in predicted state of the body. For example, if the activity is a workout, the backoff period may be five minutes before the example process 500 will return a change in state from on-body to off-body. As another example, the backoff period may be fifteen minutes if the activity is that the user is sleeping. In other implementations, the backoff period may be longer or shorter. Alternatively, the backoff period may be omitted.

Finally, the example process 500 may determine if the smoothed prediction, optionally following any backoff period, indicates that the wearable device is on-body, as in 514. If it is determined that the wearable device is on-body, the body detection process determines that a body is detected, as in 516. If it is determined that the device is off-body, the example process determines that a body is not detected, as in 518.

Figure 6:
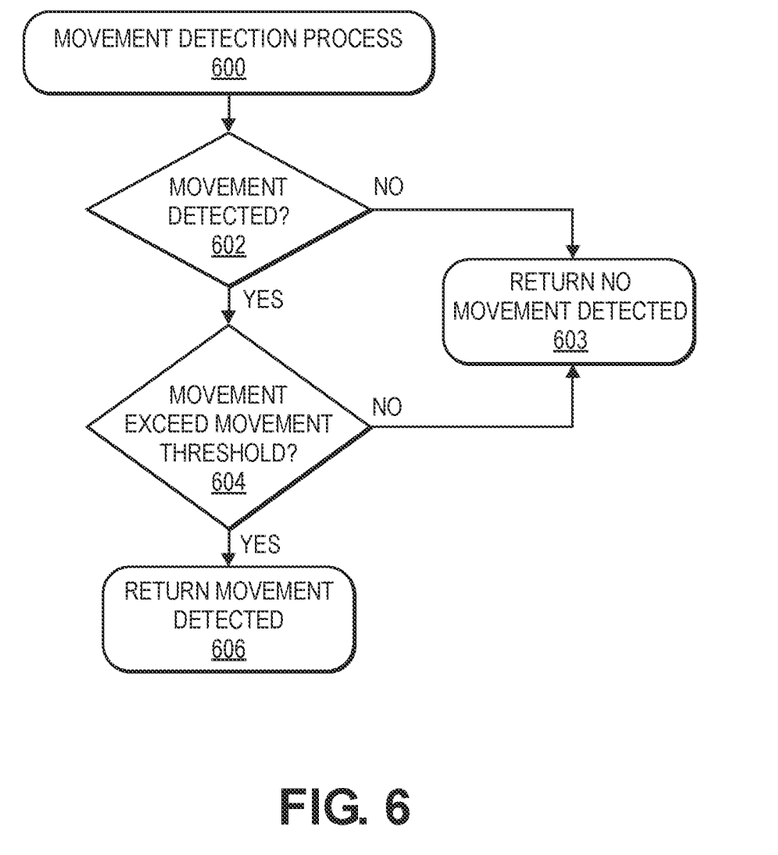
FIG. 6 is an example movement detection process, in accordance with described implementations.

FIG. 6 is an example movement detection process 600, in accordance with described implementations. The example process 600 may be continuously or periodically performed when the device is in the off-body state 312 (FIG. 3A), as discussed above, and/or at other times when movement data collection is desirable.

The example process 600 begins by determining if movement is detected, as in 602. For example, motion sensor data may be received from a motion sensor of the wearable device. As noted above, the motion sensor may be, for example but not limitation, an accelerometer, gyroscope, etc. If no movement is detected, the example process 600 may return an indication that no movement is detected, as in 603.

If movement is detected, it may be determined whether the movement exceeds a threshold, as in 604. The threshold may be any value and/or duration of time and may be different for different times of day, different devices, different device types, different users, etc. Overall, the movement threshold may be set so that slight movements or vibrations that are not indicative of the device being moved or placed on a body of the user are ignored.

If it is determined that the movement does not exceed the movement threshold, the example process may return an indication that no movement is detected, as in 603. If it is determined that movement does exceed the movement threshold, the example process may return an indication that movement has been detected, as in 606. As discussed above, detection of movement may result in the wearable device transitioning from an off-body state to a check proximity state.

Figure 7:
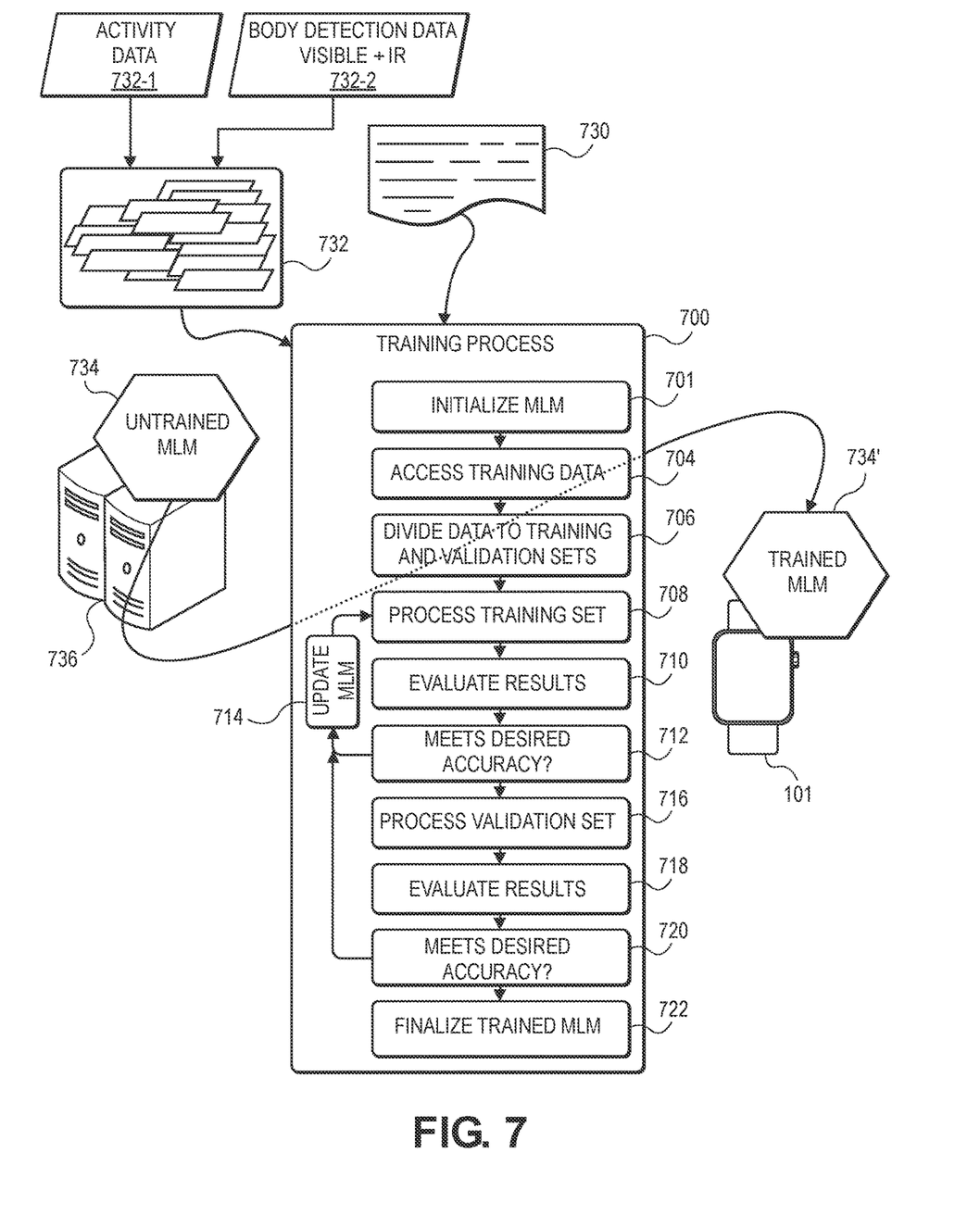
FIG. 7 is a block diagram illustrating an exemplary overall process of training a machine learning model, in accordance with described implementations.

FIG. 7 illustrates an exemplary overall process 700 of training a machine learning model in accordance with aspects of the disclosed subject matter. Indeed, as shown in FIG. 7, the training process 700 is configured to train an untrained machine learning model 734 operating on a computer system 736 to transform the untrained machine learning model into a trained machine learning model 734' that operates on the same or another computer system, such as a portable device 101. In the course of training, as shown in the training process 700, at step 701, the untrained machine learning model 734 is initialized with training criteria 730 comprising one or more of static features, dynamic features, and processing features.

At step 704 of the training process 700, a corpus 732 of training data is accessed. According to aspects of the disclosed subject matter, the corpus of training data is representative of the input data, such as activity data 732-1 and/or body detection data 732-2, which includes one or more of visible light sensor data and/or IR sensor data that the resulting, trained machine learning model 734' will receive. In various embodiments, the training data is labeled training data. Of course, in various embodiments, the corpus 732 of training data may include unlabeled training data. In some implementations, to eliminate bias in the training data, a similar amount of training data may be collected for various different skin-tones of users. As is known, the amount of visible light from a PPG sensor that is reflected based into the sensor depends on the skin tone as the melanin in the skin absorbs some of the light. Accordingly, in some implementations, darker skin-tones, which absorb more light, may be assigned a higher weighting so that the machine learning model, when trained, will be better tuned to accurately detect the state of the device on darker skin tones.

With the corpus 732 of training data accessed, at step 706 the training data is divided into training and validation sets. Generally speaking, the items of data in the training set are used to train the untrained machine learning model 734 and the items of data in the validation set are used to validate the training of the machine learning model. As those skilled in the art will appreciate, and as described below in regard to much of the remainder of the training process 700, there are numerous iterations of training and validation that occur during the training of the machine learning model.

At step 708 of the training process, the data elements of the training set are processed, often in an iterative manner. Processing the data elements of the training set include capturing the processed results. After processing the elements of the training set, at step 710, the aggregated results of processing the training set are evaluated, and at step 712, a determination is made as to whether a desired accuracy level has been achieved. If the desired accuracy level is not achieved, in step 714, aspects of the machine learning model are updated in an effort to guide the machine learning model to generate more accurate results, and processing returns to step 708. Alternatively, if the desired accuracy level is achieved, the training process 700 advances to step 716.

At step 716, and much like step 708, the data elements of the validation set are processed, and at step 718, the processing accuracy of this validation set is aggregated and evaluated. At step 720, a determination is made as to whether a desired accuracy level, in processing the validation set, has been achieved. If the desired accuracy level is not achieved, in step 714, aspects of the machine learning model are updated in an effort to guide the machine learning model to generate more accurate results, and processing returns to step 708. Alternatively, if the desired accuracy level is achieved, the training process 700 advances to step 722.

At step 722, a finalized, trained machine learning model 734' is generated. Typically, though not exclusively, as part of finalizing the now-trained machine learning model 734', portions of the machine learning model that are included in the model during training for training purposes are extracted, thereby generating a more efficient trained machine learning model 734".

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers, communications, etc., should recognize that components and process steps described herein may be interchangeable with other components or steps, or combinations of components or steps, and still achieve the benefits and advantages of the present disclosure. Moreover, it should be apparent to one skilled in the art that the disclosure may be practiced without some, or all of the specific details and steps disclosed herein. Moreover, with respect to the one or more methods or processes of the present disclosure described herein, including but not limited to the flow charts shown in FIGS. 4A through 7, orders in which such methods or processes are presented are not intended to be construed as any limitation on the claimed inventions, and any number of the method or process steps or boxes described herein can be combined in any order and/or in parallel to implement the methods or processes described herein, and/or omitted. Also, the drawings herein are not drawn to scale.

Aspects of the disclosed apparatus, method, and system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage media may be implemented by a volatile computer memory, non-volatile computer memory, hard drive, solid-state memory, flash drive, removable disk, and/or other media. In addition, components of one or more of the modules and engines may be implemented in firmware or hardware.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially," as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative implementations thereof, the foregoing and various other additions and omissions may be made therein and thereto without departing from the spirit and scope of the present disclosure.

What is claimed is:

1. A computer-implemented method, comprising:
   maintaining a first sensor and a second sensor included on a wearable device in a disabled state;
   detecting, at the wearable device, an event;
   in response to the event:
      activating the first sensor, without activating the second sensor, to collect a first sensor data;
      determining, based at least in part on the first sensor data, that the wearable device is within a defined proximity of an object;
      in response to determining that the wearable device is within the defined proximity, activating the second sensor to collect a second sensor data;
      determining, based at least in part on the second sensor data, that the object is an animate object;
      in response to determining that the object is the animate object:
         deactivating the first sensor;
         continuing to collect the second sensor data; and
         generating, based at least in part on the second sensor data, biometric data about the animate object;

while collecting the second sensor data, determining, based at least in part on the second sensor data, that the animate object is no longer detected; and in response to determining that the animate object is no longer detected:
  activating the first sensor to collect a third sensor data;
  determining, based at least in part on the third sensor data, that the wearable device is no longer within the defined proximity of the object; and in response to determining from the third sensor data that the wearable device is no longer within the defined proximity of the object:
  disabling the first sensor; and
  disabling the second sensor.

2. The computer-implemented method of claim 1, wherein:
  the first sensor is an infrared sensor; and
  the second sensor is a photoplethysmography sensor utilizing at least one of a 530 nanometer wavelength, a 645 nanometer wavelength, or a 470 nanometer wavelength.

3. The computer-implemented method of claim 1, wherein:
  the first sensor and the second sensor are part of a single sensor component; and
  activating the first sensor without activating the second sensor includes activating a first light emitting diode of the single sensor component without activating a second light emitting diode of the single sensor component.

4. The computer-implemented method of claim 1, further comprising:
  while collecting the second sensor data, determining that the wearable device has been connected to a power supply; and
  in response to determining that the wearable device has been connected to the power supply, continuing to collect at least the second sensor data.

5. A computing system, comprising:
  one or more processors; and
  a memory storing program instructions that, when executed by the one or more processors, cause the one or more processors to at least:
    maintain, during a first time, a first sensor of a device worn by a user in an active state;
    determine, based at least in part on a first sensor data of the first sensor, that an animate object is no longer determinable from the first sensor data;
    in response to a determination that the animate object is no longer determinable, collect, with a second sensor of the device, a proximity data;
    determine, based at least in part on the proximity data, that the device is within a defined proximity of an object; and
    in response to a determination that the device is within the defined proximity, continue, with the first sensor, to collect the first sensor data during a second time;
    determine, while the first sensor is in the active state and collecting the first sensor data during a first segment of the second time, that the animate object is no longer determinable from the first sensor data collected during at least a portion of the first segment of the second time;
    in response to a determination that the animate object is no longer determinable from the first sensor data collected during at least the portion of the first segment of the second time, collect, with the second sensor of the device and during the second time, a second proximity data;
    determine, based at least in part on the second proximity data, that the device is beyond the defined proximity; and
    in response to a determination that the device is beyond the defined proximity, disable the first sensor and the second sensor.

6. The computing system of claim 5, wherein the program instructions that, when executed by the one or more processors, further cause the one or more processors to at least:
  continue, during a third time that is subsequent to the second time, to collect the second proximity data; and
  determine, based at least in part on the second proximity data, that the device is beyond the defined proximity; and
  wherein disabling the first sensor and the second sensor is after the third time and in response to a determination that the device is beyond the defined proximity.

7. The computing system of claim 6, wherein a duration of the third time is based at least in part on an activity determined for the user.

8. The computing system of claim 5, wherein the program instructions that, when executed by the one or more processors, further cause the one or more processors to at least:
  determine, while the first sensor is in the active state and collecting the first sensor data during a second segment of the second time, that the animate object is no longer determinable from the first sensor data collected during at least a portion of the second segment of the second time, wherein the second segment of the second time precedes the first segment of the second time;
  in response to a determination that the animate object is no longer determinable from the first sensor data collected during at least the portion of the second segment of the second time, collect, with the second sensor of the device and during the second time, a second proximity data;
  determine, based at least in part on the second proximity data, that the device is beyond the defined proximity;
  determine, based at least in part on the second proximity data, that the device is not beyond a second defined proximity that is larger than the defined proximity; and
  in response to a determination that the device is beyond the defined proximity and not beyond the second defined proximity, continue, with the first sensor, to collect the first sensor data during the second time.

9. The computing system of claim 5, wherein the program instructions that, when executed by the one or more processors, further cause the one or more processors to at least:
  determine, during the second time, that the device is connected to a charger.

10. The computing system of claim 9, wherein the program instructions that, when executed by the one or more processors, further cause the one or more processors to at least:
  in response to a determination that the device is connected to the charger, collect, with the second sensor of the device, a second proximity data;
  determine, based at least in part on the second proximity data, that the device is within the defined proximity; and
  in response to a determination that the device is within the defined proximity, continue, with the first sensor, to collect the first sensor data during a third the second time.

11. A computing system, comprising:
one or more processors; and
a memory storing program instructions that, when executed by the one or more processors, cause the one or more processors to at least:
  maintain, during a first time, a first sensor of a device worn by a user in an active state;
  determine, based at least in part on a first sensor data of the first sensor, that an animate object is no longer determinable from the first sensor data;
  in response to a determination that the animate object is no longer determinable, collect, with a second sensor of the device, a proximity data;
  determine, based at least in part on the proximity data, that the device is within a defined proximity of an object; and
  in response to a determination that the device is within the defined proximity, continue, with the first sensor, to collect the first sensor data during a second time;
determine, while the first sensor is in the active state and collecting the first sensor data during the second time, that the animate object is no longer determinable from the first sensor data collected during at least a portion of the second time;
in response to a determination that the animate object is no longer determinable from the first sensor data collected during at least the portion of the second time, collect, with the second sensor of the device and during the second time, a second proximity data;
determine, based at least in part on the second proximity data, that the device is beyond the defined proximity;
determine, based at least in part on the second proximity data, that the device is beyond a second defined proximity that is larger than the defined proximity; and
in response to a determination that the device is beyond the defined proximity and beyond the second defined proximity, disable the first sensor and the second sensor.

12. An apparatus, comprising:
a first light emitting diode ("LED");
a second LED that is different than the first LED;
one or more processors; and
a memory storing program instructions that, when executed by the one or more processors, cause the one or more processors to at least:
  receive, from the first LED, a first sensor data indicative of a proximity of the apparatus to an object;
  determine, based at least in part on the first sensor data, that the apparatus is within a defined proximity of the object;
  in response to a determination that the apparatus is within the defined proximity of the object, collect second sensor data corresponding to the second LED;
  segment the second sensor data to produce a plurality of segments of the second sensor data;
  process, with a machine learning model, the second sensor data at least one segment of the plurality of segments to determine that the second sensor data corresponds to an animate object;
  in response to a determination that the second sensor data at least one segment corresponds to the animate object, continue to collect the second sensor data; and
  generate, with the second sensor data, biometric data corresponding to the animate object.

13. The apparatus of claim 12, wherein the program instructions that, when executed by the one or more processors, further cause the one or more processors to at least:
  normalize and compress the at least one segment of the plurality of segments to produce a processed sample; and
  wherein the machine learning model processes the at least one segment of the plurality of segments as the processed sample.

14. The apparatus of claim 13, wherein:
the machine learning model processes the processed sample to determine a predicted state of the apparatus; and
the program instructions that, when executed by the one or more processors to determine that the second sensor data corresponds to the animate object, further include instructions that, when executed by the one or more processors, further cause the one or more processors to at least:
  apply a hysteresis to the predicted state to produce a class label;
  filter the class label to produce a smoothed sample; and
  determine, based at least in part on the smoothed sample, that the second sensor data corresponds to the animate object.

15. The apparatus of claim 12, further comprising:
a motion sensor; and
wherein the program instructions that, when executed by the one or more processors, further cause the one or more processors to at least:
  determine, based on motion sensor data received from the motion sensor, a movement of the apparatus; and
  in response to the movement, activate the first LED.

16. The apparatus of claim 15, wherein the program instructions that, when executed by the one or more processors, further cause the one or more processors to at least:
  determine that the movement exceeds a threshold; and
  wherein the first LED is activated in response to a determination that the movement exceeds the threshold.

17. The apparatus of claim 12, wherein the program instructions that, when executed by the one or more processors, further cause the one or more processors to at least:
  while collecting the second sensor data, determine, based at least in part on the second sensor data, that the animate object is no longer detected; and
  in response to determination that the animate object is no longer detected:
    activate the first LED to collect a third sensor data;
    determine, based at least in part on the third sensor data, that the apparatus is no longer within the defined proximity of the object; and
    in response to determination from the third sensor data, that the apparatus is no longer within the defined proximity of the object, disable the second LED.

18. The apparatus of claim 12, wherein the program instructions that, when executed by the one or more processors, further cause the one or more processors to at least:
  determine, while the second LED is collecting the first sensor data, that the animate object is no longer determinable from the first sensor data;
  in response to a determination that the animate object is no longer determinable from the first sensor data, collect, with the first LED of the apparatus, a second proximity data;

determine, based at least in part on the second proximity data, that the apparatus is beyond the defined proximity; and in response to a determination that the apparatus is beyond the defined proximity, disable the first LED and the second LED.

19. The apparatus of claim 12, wherein the program instructions that, when executed by the one or more processors, further cause the one or more processors to at least:

in response to a determination that the at least one segment of the plurality of segments corresponds to the animate object, deactivate the first LED sensor.

20. The apparatus of claim 12, wherein the program instructions that, when executed by the one or more processors, further cause the one or more processors to at least:

determine that the device is connected to a charger; and in response to determination that the device is connected to the charger, continue to collect the second sensor data.

\* \* \* \* \*